US009962296B2

(12) United States Patent
Mansfield

(10) Patent No.: US 9,962,296 B2
(45) Date of Patent: May 8, 2018

(54) ABSORBENT ARTICLE WITH TEAR RESISTANT FILM

(71) Applicant: The Procter & Gamble Company, Cincinnati, OH (US)

(72) Inventor: Todd Leon Mansfield, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 550 days.

(21) Appl. No.: 14/634,927

(22) Filed: Mar. 2, 2015

(65) Prior Publication Data
US 2015/0173960 A1 Jun. 25, 2015

Related U.S. Application Data

(60) Continuation of application No. 14/085,846, filed on Nov. 21, 2013, now Pat. No. 9,000,253, which is a
(Continued)

(51) Int. Cl.
*A61F 13/49* (2006.01)
*A61F 13/15* (2006.01)
(Continued)

(52) U.S. Cl.
CPC ........ *A61F 13/15203* (2013.01); *A61F 13/42* (2013.01); *A61F 13/4902* (2013.01); *A61F 13/496* (2013.01); *A61F 13/49015* (2013.01); *A61F 13/513* (2013.01); *A61F 13/5116* (2013.01); *A61F 13/51458* (2013.01); *A61F 13/51464* (2013.01); *A61F 13/51478* (2013.01); *A61F 13/565* (2013.01); *A61L 15/24* (2013.01); *A61L 15/42* (2013.01); *A61L 15/56* (2013.01); *A61L 15/62* (2013.01); *B32B 3/266* (2013.01); *B32B 5/022* (2013.01); *B32B 5/26* (2013.01); *B32B 7/14* (2013.01); *B32B 27/12* (2013.01); *B32B 27/302* (2013.01); *C08L 53/025* (2013.01); *A61F 2013/15292* (2013.01);
(Continued)

(58) Field of Classification Search
CPC ...... A61F 2013/15292; A61F 13/15203; A61F 13/42; A61F 13/49015; A61F 13/4902; A61F 13/496; A61F 13/5116; A61F 13/513; A61F 13/51458; A61F 13/51464; A61F 13/51478; A61F 13/565; A61F 2013/51165; A61F 2013/51322
See application file for complete search history.

(56) References Cited

U.S. PATENT DOCUMENTS 3,848,594 A 11/1974 Buell
3,860,003 A 1/1975 Buell
(Continued)

FOREIGN PATENT DOCUMENTS

WO WO 1995/016746 A1 6/1995

OTHER PUBLICATIONS

International Search Report, PCT/US2012/024986, dated Jun. 21, 2012 (13 pages).

*Primary Examiner* — Susan Su
(74) *Attorney, Agent, or Firm* — Wednesday G. Shipp

(57) ABSTRACT

A disposable absorbent article that includes an elastic film material. The elastic film resists the growth of a tear and include an SEEPS block copolymer having a $T_m$ of between about 10° C. and about 20° C. The film has a time-to-fail of greater than 1 hour.

16 Claims, 4 Drawing Sheets

Related U.S. Application Data division of application No. 13/026,563, filed on Feb. 14, 2011, now Pat. No. 8,618,350.

(51) Int. Cl.

| | | |
|---|---|---|
| C08L 53/02 | (2006.01) | |
| A61F 13/496 | (2006.01) | |
| A61F 13/42 | (2006.01) | |
| A61L 15/24 | (2006.01) | |
| A61L 15/56 | (2006.01) | |
| A61L 15/62 | (2006.01) | |
| B32B 5/02 | (2006.01) | |
| B32B 5/26 | (2006.01) | |
| B32B 7/14 | (2006.01) | |
| B32B 27/12 | (2006.01) | |
| B32B 27/30 | (2006.01) | |
| B32B 3/26 | (2006.01) | |
| A61F 13/56 | (2006.01) | |
| A61F 13/511 | (2006.01) | |
| A61F 13/513 | (2006.01) | |
| A61F 13/514 | (2006.01) | |
| A61L 15/42 | (2006.01) | |

(52) U.S. Cl.
CPC ........... *A61F 2013/51165* (2013.01); *A61F 2013/51322* (2013.01); *B32B 2250/03* (2013.01); *B32B 2250/05* (2013.01); *B32B 2250/40* (2013.01); *B32B 2274/00* (2013.01); *B32B 2307/51* (2013.01); *B32B 2307/54* (2013.01); *B32B 2307/5825* (2013.01); *B32B 2555/02* (2013.01)

(56) References Cited

U.S. PATENT DOCUMENTS

| | | |
|---|---|---|
| 4,610,678 A | 9/1986 | Weisman et al. |
| 4,662,875 A | 5/1987 | Hirotsu et al. |
| 4,673,402 A | 6/1987 | Weisman et al. |
| 4,699,622 A | 10/1987 | Toussant et al. |
| 4,808,178 A | 2/1989 | Aziz et al. |
| 4,834,735 A | 5/1989 | Alemany et al. |
| 4,834,741 A | 5/1989 | Sabee |
| 4,846,815 A | 7/1989 | Scripps |
| 4,888,231 A | 12/1989 | Angstadt |
| 4,894,060 A | 1/1990 | Nestegard |
| 4,909,803 A | 3/1990 | Aziz et al. |
| 4,940,464 A | 7/1990 | Van Gompel et al. |
| 4,946,527 A | 8/1990 | Battrell |
| 4,963,140 A | 10/1990 | Robertson et al. |
| 4,980,114 A | 12/1990 | Satake et al. |
| 5,032,120 A | 7/1991 | Freeland et al. |
| 5,092,861 A | 3/1992 | Nomura et al. |
| 5,137,537 A | 8/1992 | Herron et al. |
| 5,147,345 A | 9/1992 | Young et al. |
| 5,151,092 A | 9/1992 | Buell et al. |
| 5,159,532 A | 10/1992 | Kilian et al. |
| 5,221,274 A | 6/1993 | Buell et al. |
| 5,242,436 A | 9/1993 | Weil et al. |
| 5,246,433 A | 9/1993 | Hasse et al. |
| 5,260,345 A | 11/1993 | Desmarais et al. |
| 5,342,388 A | 8/1994 | Toller |
| 5,387,207 A | 2/1995 | Dyer et al. |
| 5,397,316 A | 3/1995 | Lavon et al. |
| 5,464,401 A | 11/1995 | Hasse et al. |
| 5,499,978 A | 3/1996 | Buell et al. |
| 5,507,736 A | 4/1996 | Clear et al. |
| 5,531,732 A | 7/1996 | Wood |
| 5,554,145 A | 9/1996 | Roe et al. |
| 5,569,234 A | 10/1996 | Buell et al. |
| 5,571,096 A | 11/1996 | Dobrin et al. |
| 5,580,411 A | 12/1996 | Nease et al. |
| 5,591,152 A | 1/1997 | Buell et al. |
| 5,607,760 A | 3/1997 | Roe |
| 5,609,587 A | 3/1997 | Roe |
| 5,625,222 A | 4/1997 | Yoneda et al. |
| 5,635,191 A | 6/1997 | Roe et al. |
| 5,643,588 A | 7/1997 | Roe et al. |
| 5,693,711 A | 12/1997 | Akiba et al. |
| 5,773,517 A | 6/1998 | Masuda et al. |
| 5,843,056 A | 12/1998 | Good et al. |
| 5,865,823 A | 2/1999 | Curro |
| 5,885,908 A | 3/1999 | Jaeger et al. |
| 5,897,545 A | 4/1999 | Kline et al. |
| 5,957,908 A | 9/1999 | Kline et al. |
| 6,004,306 A | 12/1999 | Robles et al. |
| 6,096,435 A | 8/2000 | Maekawa et al. |
| 6,107,537 A | 8/2000 | Elder et al. |
| 6,120,487 A | 9/2000 | Ashton |
| 6,120,489 A | 9/2000 | Johnson et al. |
| 6,299,607 B1 | 10/2001 | Osborn et al. |
| 6,307,120 B1 | 10/2001 | Glaug |
| 6,420,475 B1 | 7/2002 | Chen |
| 6,432,098 B1 | 8/2002 | Kline et al. |
| 6,472,084 B1 | 10/2002 | Middlesworth et al. |
| 6,772,708 B2 | 8/2004 | Klofta et al. |
| 6,794,440 B2 | 9/2004 | Chen |
| 6,904,865 B2 | 6/2005 | Klofta et al. |
| 6,942,748 B2 | 9/2005 | Cree et al. |
| 7,033,675 B2 | 4/2006 | Taniguchi et al. |
| 7,067,583 B2 | 6/2006 | Chen |
| 7,105,715 B2 | 9/2006 | Carlucci et al. |
| 7,332,642 B2 | 2/2008 | Liu |
| 7,527,616 B2 | 5/2009 | Miyamoto |
| 7,626,073 B2 | 12/2009 | Catalan |
| 7,744,576 B2 | 6/2010 | Busam et al. |
| 7,750,203 B2 | 7/2010 | Becker et al. |
| 7,833,211 B2 | 11/2010 | Mansfield |
| 8,618,350 B2 | 12/2013 | Mansfield |
| 2002/0040213 A1 | 4/2002 | Tweddell, III et al. |
| 2003/0109843 A1 | 6/2003 | Gibbs |
| 2003/0109844 A1 | 6/2003 | Gibbs |
| 2003/0130407 A1 | 7/2003 | Chen |
| 2006/0147716 A1 | 7/2006 | Braverman et al. |
| 2006/0148354 A1 | 7/2006 | Shelley et al. |
| 2006/0246803 A1 | 11/2006 | Smith et al. |
| 2007/0141311 A1 | 6/2007 | Mleziva et al. |
| 2007/0155900 A1 | 7/2007 | Chang et al. |
| 2008/0177242 A1 | 7/2008 | Chang et al. |
| 2008/0306214 A1 | 12/2008 | Kanderski |
| 2009/0247703 A1 | 10/2009 | Handlin |
| 2009/0258210 A1 | 10/2009 | Iyad et al. |
| 2010/0312207 A1 | 12/2010 | Rezai et al. |
| 2012/0123367 A1 | 5/2012 | Melik et al. |
| 2012/0207969 A1 | 8/2012 | Mansfield |
| 2012/0207996 A1 | 8/2012 | Chapman et al. |
| 2012/0208420 A1 | 8/2012 | Mansfield |
| 2012/0209230 A1 | 8/2012 | Mansfield |
| 2014/0081228 A1 | 3/2014 | Mansfield |

# ABSORBENT ARTICLE WITH TEAR RESISTANT FILM

FIELD OF THE INVENTION

The present application is directed, generally, to an absorbent article that includes an improved elastic film material. Specifically, there is disclosed an absorbent article and/or component(s) thereof that include a film exhibiting improved resistance to the undesired growth of a tear, hole, aperture, or other discontinuity.

BACKGROUND OF THE INVENTION

Absorbent articles are widely used to receive and store liquid contaminants for disposal. Commonly known absorbent articles include diapers, pull-on, pant-type diapers, adult incontinence articles, sanitary napkins, and panty liners. It is not uncommon for absorbent articles to include film materials, especially elastic films, to control the movement of liquids and provide a comfortable, conforming fit when the article is worn by a wearer. However, conventional elastic film materials have been known to form holes or tears when subjected to the normal wear and tear of the article when in use. Such damage may be related to, for example, material defects, contact with sharp objects, pulling and stretching by a wearer, rigorous activity of a wearer, and/or repetitive mechanical stress experienced during wear. Additionally, it is not uncommon for film materials incorporated into disposable absorbent articles to be subjected to vigorous mechanical and/or thermal stress during various manufacturing processes (e.g., incremental stretching processes or bonding processes such as high pressure bonding, thermal bonding, and ultrasonic bonding), which may result in undesirable tears and/or holes in the film. In certain applications, it may even be desirable to intentionally include in a disposable absorbent article a film that has one or more pre-formed discontinuities (e.g., one or more apertures that extend at least partially through the thickness of the film), for example, to control the breathability, permeability to liquids and/or solids, opacity, and/or extensibility of the article or article component.

Initially, openings in the film, whether desired or undesired, may start out small and be relatively inconsequential with regard to the desired function of the film, article component and/or article. But as the size of the opening grows, it may ultimately lead to partial or complete (catastrophic) failure of the film, article component and/or article. Unintended catastrophic failure of an article or article component is almost always undesirable, but when the article is a disposable absorbent article such as a diaper or training pant, the consequences of catastrophic failure of the article or component may be especially acute due to, for example, the possibility of bodily exudates escaping from the article and/or the article separating from the wearer. To further compound the potential problems associated with conventional films, at least some manufacturers desire to use thinner and/or lower basis weight films to reduce material costs. The aforementioned problems associated with the formation of tears, holes, and apertures in a film may be even more acute in thinner/lower basis weight films.

To reduce the possibility that an elastic film will fail due to the presence and/or formation of tear, hole, and/or aperture, the strength of the film may be increased. Increasing the strength of the film typically means increasing the thickness of the film or forming the film from different materials, both of which may undesirably impact the cost and/or complexity of manufacturing the film or the suitability of the film for a particular use. For example, using a stronger film in an absorbent article such as a diaper or pant may result in an undesirable amount of pressure being applied to the skin of a wearer, which may lead to red-marking and/or discomfort. Additionally, increasing the overall strength of the film may only improve the film's resistance to the initial formation of a hole, tear, or aperture and not its subsequent growth.

Another method for reducing the possibility of undesired growth of a tear, hole, or aperture in a film, especially in a low basis weight film, includes joining one or more reinforcing layers to the film. For example, the film may be sandwiched between two or more nonwoven layers and/or the film may be formed with one or more commonly known "skin layers" (e.g., through a co-extrusion process). However, adding additional layers of material to improve the performance of the film may undesirably increase the cost and/or complexity of producing a particular article or article component that incorporates the film and/or make the film unsuitable for its intended purpose. Thus, there remains a need to provide a film suitable for use in an absorbent article that exhibits resistance to the growth of tears, holes, and/or apertures in a variety of circumstances (e.g., at a low basis weight) without the use of additional reinforcing materials.

Accordingly, it would be desirable to provide an absorbent article that includes a film having an improved resistance to the growth of a tear, hole, or aperture.

SUMMARY OF THE INVENTION

In order to provide a solution to the problems set forth above, a disposable absorbent article comprising an elastic film material that resists the growth of a tear is disclosed. The elastic film material comprises an SEEPS block copolymer having a $T_m$ of between about 10° C. and about 20° C. The film has a time-to-fail of greater than about 1 hour according to the Slow Tear Test.

DETAILED DESCRIPTION OF THE INVENTION

Definitions

Figure 1:
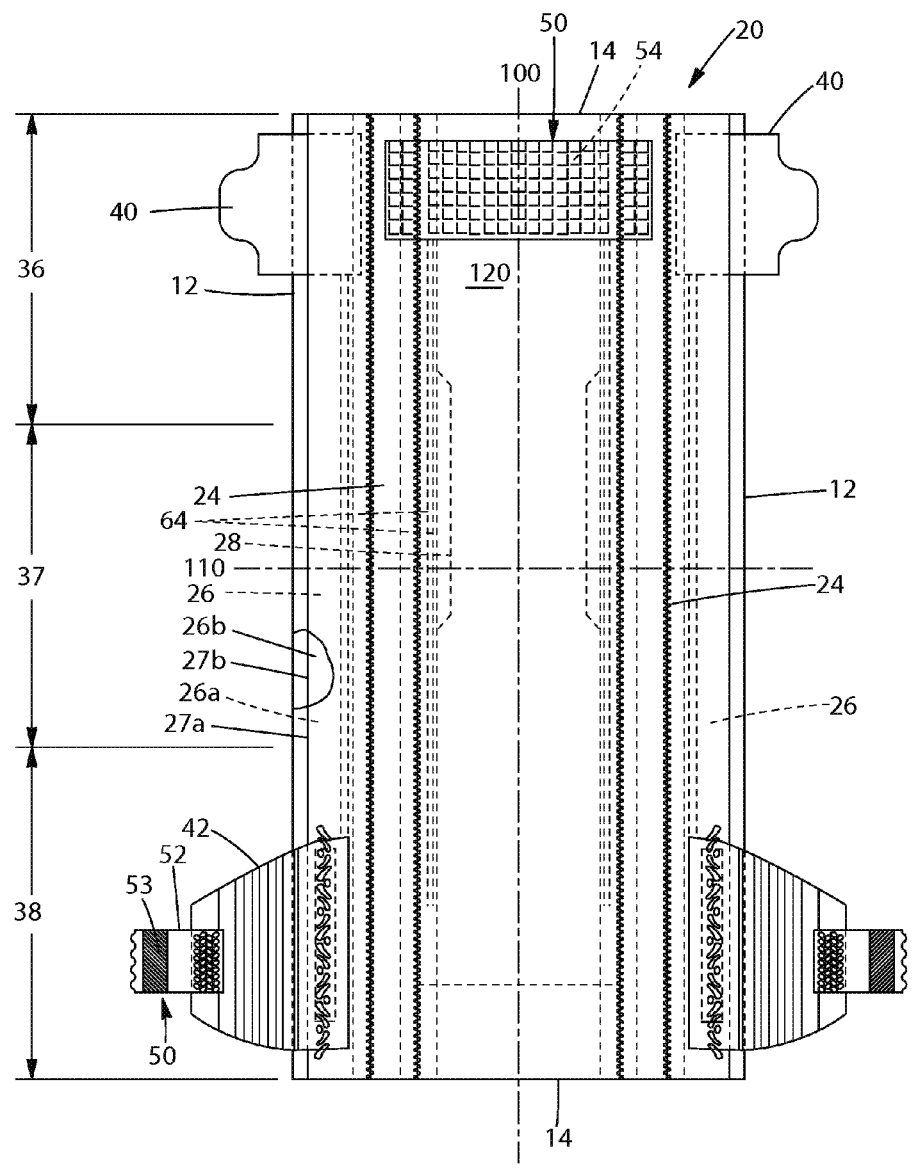
FIG. 1 is a plan view of an absorbent article.

"Absorbent article" means a device that absorbs and contains body exudates and, more specifically, devices that are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Activation" is the mechanical deformation of a plastically extensible material that results in permanent elongation of the extensible material in the direction of activation in the X-Y plane of the material. For example, activation occurs when a web or portion of a web is subjected to a stress that causes the material to strain beyond the onset of plasticity, which may or may not include complete mechanical failure of the material or portion of the material. Activation of a laminate that includes an elastic material joined to a plastically extensible material typically results in permanent deformation of the plastic material, while the elastic material returns substantially to its original dimension. "Activate," and variations thereof, means subjecting a material to an activation process.

"Aperture" means an opening in a film purposefully added during filmmaking or laminate making, which is intended to impart a desired characteristic such as breathability. The growth of an aperture is the increase in the size of the aperture due to mechanical failure of the portion(s) of the film adjacent to the aperture.

"Basis weight" is the property of a sheet or web of material calculated as the mass of the material divided by its surface area. The units for basis weight herein are grams per square meter ($g/m^2$).

"Breathable" means a film or laminate that give Air Permeability Values of between 5 and 50 $m^3/m^2/min$ in the Air Permeability Test described below.

"Copolymer" means a polymer derived from two or more monomer species wherein the polymer chains each comprise repeat units from more than one monomer species.

"Crystalline melting temperatures" are determined by Differential Scanning calorimetry, which is described in more detail below. The melting endothermic peak temperature is taken as the $T_m$ ($T_{pm}$ per ASTM D3418-08) of a particular population of crystals. Materials of the current invention may have one or more melting endotherm peaks.

"Disposed" means an element is positioned in a particular place with regard to another element.

"Elastic," "elastomeric," and "elastically extensible" mean the ability of a material to stretch by at least 50% without rupture or breakage at a given load, and upon release of the load the elastic material or component exhibits at least 80% recovery (i.e., has less than 20% set). For example, an elastic material that has an initial length of 100 mm can stretch to at least 150 mm (50% stretch) and, upon removal of the force, retract to a length of 110 mm (i.e., have a set of 10 mm or 10%). Stretch, sometimes referred to as strain, percent strain, engineering strain, draw ratio, or elongation, along with recovery and set may each be determined according to the Hysteresis Test described in more detail below. It is to be understood; however, that this definition of elastic does not apply to materials that do not have the proper dimensions (e.g., not wide enough) to be properly subjected to the Hysteresis Test. Instead, such material is considered to be elastic if it can stretch to at least 50% upon application of a biasing force, and return substantially to its original length (i.e., exhibit less than 20% set) upon release of the biasing force.

"Extensible" means the ability to stretch or elongate, without rupture or breakage, by at least 50%.

"Film" means a sheet-like material wherein the length and width of the material far exceed the thickness of the material (e.g., 10×, 50×, or even 1000× or more). Films are typically liquid impermeable but may be configured to be breathable.

"Hole" means an unwanted opening in a film that tends to act as a "crack" in the Fracture Mechanics sense. Mechanical failure of the film may result from the growth of a hole. The growth of a hole is the increase in the size of the hole due to mechanical failure of the portion(s) of the film adjacent to the hole.

"Joined" means configurations whereby an element is directly secured to another element by affixing the element directly to the other element, and configurations whereby an element is indirectly secured to another element by affixing the element to intermediate member(s) that in turn are affixed to the other element.

"Laminate" means two or more materials that are bonded to one another by any suitable method known in the art (e.g., adhesive bonding, thermal bonding, ultrasonic bonding, or high pressure bonding using non-heated or heated patterned roll).

"Longitudinal" means a direction running substantially perpendicular from a waist end edge to an opposing waist end edge of an absorbent article when the article is in a flat out, uncontracted state, or from a waist end edge to the bottom of the crotch in a bifolded article. Directions within 45 degrees of the longitudinal direction are considered to be "longitudinal." "Lateral" refers to a direction running from a side edge to an opposing side edge of an article and generally perpendicular to the longitudinal direction. Directions within 45 degrees of the lateral direction are considered lateral.

"Machine direction" or "MD" is the direction parallel to the direction of travel of the web in a manufacturing process. Directions within 45 degrees of the MD are considered to be machine directional. The "cross machine direction" or "CD" is the direction substantially perpendicular to the MD and in the plane generally defined by the web. Directions within 45 degrees of the CD are considered to be cross directional.

"Nonwoven" means a porous, fibrous material made from continuous (long) filaments (fibers) and/or discontinuous (short) filaments (fibers) by processes such as, for example, spunbonding, meltblowing, airlaying, carding, coforming, hydroentangling, and the like. Nonwovens do not have a woven or knitted filament pattern. Nonwovens may be liquid permeable or impermeable.

"Plastic" and "plastically extensible" mean the ability of a material to stretch by at least 50% without rupture or breakage at a given load and, upon release of the load the material or component, exhibits at least 20% set (i.e., recovers less than 80%). For example, an extensible material that has an initial length of 100 mm can stretch at least to 150 mm (50% stretch) and, upon removal of the applied force, retract to a length of 35 mm (i.e., have a set of 35 mm (35% set), when subjected to a suitable hysteresis test commonly known in the art.

"Relaxed" means the state of an element, material or component at rest with substantially no external force acting on the element, other than gravity.

"Tear" means an undesired opening in a film that has intersected with one or more of the edges of the film, which can act as a "crack" in the Fracture Mechanics sense. The growth of a tear is the increase in the size of the tear due to mechanical failure of the portion(s) of the film adjacent to the tear.

"Web" means a material capable of being wound into a roll. Webs may be films, nonwovens, laminates, apertured films and/or laminates, and the like. The face of a web refers to one of its two dimensional surfaces, as opposed to its edge.

"X-Y plane" means the plane defined by the MD and CD of a moving web or the length and width of a piece of material.

Polymer

A number of elastomeric polymers can be used to make an elastic film. Nonlimiting examples of elastomeric polymers include homopolymers, block copolymers, random copolymers, alternating copolymers, graft copolymers, and the like. Particularly suitable polymers for use in films exhibiting resistance to tear propagation are block copolymers, which are typically made of blocks (or segments) of distinct repeat units that each contribute to the properties of the polymer. One reason block copolymers are recognized as being useful, at least in part, is because the blocks of the copolymer are covalently bonded to one another and form microphase-separated structures with rubber domains that provide good extensibility while the glassy end block domains provide mechanical integrity (e.g., good mechanical strength and avoidance of unwanted stress relaxation or flow.). Block copolymers suitable for use herein may exhibit both elastomeric and thermoplastic characteristics. For example, the end-blocks may form domains that display stiff, rigid mechanical properties at temperatures that prevail during end use (e.g., 20-40° C.), thereby adding rigidity and strength to the entire polymer. Such an end-block is sometimes referred to as a "hard block". The midblock may accommodate the relatively large deformations associated with elastomers and provides retractive force when the material is strained (i.e., stretched or extended). Such a midblock is sometimes referred to as a "soft block" or "rubbery block." Suitable block copolymers for use herein include at least one hard block (A) and at least one soft block (B). The block copolymers may have multiple blocks. In certain embodiments, the block copolymer may be an A-B-A triblock copolymer, an A-B-A-B tetrablock copolymer, or an A-B-A-B-A pentablock copolymer. Other suitable copolymers include triblock copolymers having endblocks A and A', wherein A and A' are derived from different compounds. In certain embodiments, the block copolymers may having more than one hard block and/or more than one soft block, wherein each hard block may be derived from the same or different monomers and each soft block may be derived from the same or different monomers.

Suitable hard block components have a glass transition temperature ($T_g$) greater than 25° C. or 45° C. or even 65° C., but typically less than 100° C. The hard block portion may be derived from vinyl monomers including vinyl arenes such as styrene and alpha-methyl-styrene or combinations thereof. The soft block portion may be a polymer derived from conjugated aliphatic diene monomers. Typically, the soft block monomers contain fewer than 6 carbon atoms. Suitable diene monomers such as, for example, butadiene and isoprene may be used as-polymerized or in their hydrogenated form. Suitable soft block polymers include poly(butadiene), poly(isoprene), and copolymers of ethylene/propylene, ethylene/butene, and the like. In certain embodiments, it may be desirable to partially or fully hydrogenate any residual olefinic double bonds contained in the copolymer or portion thereof (e.g., midblock or endblock).

In a particularly suitable embodiment, the elastomeric polymer may be a styrene-ethylene-ethylene-propylene-styrene ("SEEPS") block copolymer that includes two polystyrene endblocks of approximately 8 kg/mole each and a 45 kg/mole midblock. The midblock may be formed, for example, by copolymerizing and then hydrogenating isoprene and butadiene. It may be desirable to hydrogenate the copolymer such that from 95-99% or even 98-99% of the original C=C double bonds in the midblock are saturated but the polystyrene endblocks remain aromatically intact. If the degree of hydrogenation is too low, the polymer may begin to lose its ability to undergo strain-induced crystallization. It is believed, without being limited by theory, that strain induced crystallization in a polymer is important for providing tear resistant characteristics to films made with such polymers. In certain embodiments, copolymerizing isoprene and butadiene to produce the rubbery midblock may result in a copolymer that varies both in comonomer sequence and in vinyl content. While a SEEPS copolymer is a block copolymer, the ethylene-ethylene-propylene ("EEP") midblock is more of a random copolymer than blocky or alternating. But subtle departures from randomness may occur. The departures from randomness, as well as the vinyl content of the copolymer, may be controlled by adjusting the conditions during polymerization. For example, copolymerization of isoprene and butadiene with subsequent hydrogenation may give rise to a variety of branch types. Table 1 below exemplifies the different branch types that may result. With the partial exception of the methyl branches, the branches typically do not "fit" into the polyethylene-type crystals, and therefore decrease the midblock's degree of crystallinity and $T_m$. For example, the midblock of a SEEPS block copolymer may be approximately 7% crystalline at temperatures below −50° C. and have a $T_m$ of approximately 0° C. In comparison, a substantially unbranched polyethylene is approximately 75% crystalline and has a $T_m$ of approximately 135° C.

TABLE 1

| Isomer | Branch Type After Hydrogenation |
| --- | --- |
| 1,2 Isoprene | Methyl, Ethyl |
| 3,4 Isoprene | Isopropyl |
| 1,4 Isoprene | Methyl |
| 1,2 Butadiene | Ethyl |
| 1,4 Butadiene | No branch - possible to crystallize |

The length of the runs of crystallizable $CH_2$ sequences, which directly impact the melting temperature of the polymer midblock, depends, at least partially, on the sequence of comonomer incorporation into the midblock (e.g., isoprene always gives a branch of some type) and the overall balance between 1,4 and 1,2 (or 3,4) polymerization of the dienes. The $T_m$ of the crystal may provide information about the length of the crystallizable sequences and the ability of the material to undergo strain-induced crystallization, both of which are related to the number, type, and distribution of the branches on the midblock backbone. Suitable elastomers herein include sufficiently long crystallizable sequences of $CH_2$ groups (which form polyethylene-type crystals) that have a $T_m$ of greater than 10° C. (compared to, e.g., −5° C. for previously known materials). A suitable $T_m$ for the elastomers herein is between 10° C. and 20° C., 12° C. and 18° C.; 13° C. and 17° C.; or even between 14° C. and 16° C.

In addition to the EEP midblocks described above, it may be desirable to provide a midblock of the "EB" type (i.e., hydrogenated polybutadiene) that contains similar crystallizable sequences, for example, by choosing the appropriate solvent polarity (which controls 1-4 vs. 1-2 content), as described in *Anionic Polymerization: Principles and Practical Applications*, Henry Hsieh, Roderick Quirk; Chapter 9, p 197-229; Marcel Decker, New York (1996).

Film

Unlike conventional elastomeric films (e.g., films formed from known elastomers such as Vector 4211 from Dexco Polymers L.P., Houston, Tex.), which form films that exhibit minimal or no tear resistance, the elastic films disclosed herein include an effective amount of at least one elastic polymer that imparts suitable tear resistance to the film. It is to be appreciated that such resistance is not limited to tears, but also includes slits, apertures, openings, holes, and/or any other discontinuities in the film. The Slow Tear Test set forth in copending U.S. Ser. No. 13/026,533, titled "Tear Resistant Film," filed by Mansfield, on Feb. 14, 2011, provides a method for quantifying a film's resistance to the growth of a tear, hole, aperture, or other discontinuity. Suitable time-to-fail values for the films disclosed herein are greater than 1 hour, 2 hours, 4 hours, 6 hours, 10 hours, 15 hours, or even up to 24 hours or more, for example up to 30 hours, 36 hours, 40 hours, 44 hours, 48 hours, or even up to 60 hours when measured according to the Slow Tear Test. Ideally, the film is capable of resisting the growth of a tear indefinitely. While the present films desirably provide suitable resistance to the growth of a tear as described herein, it may also be desirable for the films herein to exhibit resistance to the rapid application of a relatively high amount of mechanical stress. For example, the present films may have a High-Speed Tensile Strength of between 10 and 25 MPa; 15 and 20 MPa; 16 and 19 MPa; or even between 17 and 18 MPa when measured according to the High Speed Tensile Test set forth in the aforementioned copending application titled "Tear Resistant Film." It may further be desirable to provide a film that exhibits a Notched High Speed Tensile Strength of between 10 and about 20; MPa; 14 and 19 MPa; or even between 15 and 18 MPa when measured according to the Notched High-Speed Tensile Strength Test set forth in the aforementioned copending application titled "Tear Resistant Film." It is believed, without being limited by theory, that suitable High Speed Tensile and/or Notched Tensile Strengths in a film may be important for providing at least some resistance to film failure related to relatively high rates of undesired mechanical stress.

The present tear resistant films are not limited to any particular dimension, and may be configured as relatively thin sheets of material. In certain embodiments, the film may have an Effective Average Thickness of between 1 μm-1 mm; 3 μm-1 500 μm; or 5 μm-100 μm, or any value in these ranges. The tear resistant films may be formed by any suitable method in the art such as, for example, extruding a molten thermoplastic and/or elastomeric polymer through a slit die and subsequently cooling the extruded sheet. Other non-limiting examples for making films include casting, blowing, solution casting, calendering, and formation from aqueous or cast, non-aqueous dispersions. Suitable methods of producing films from polymeric materials are described in *Plastics Engineering Handbook of the Society of the Plastics Industry, Inc.*, Fourth Edition, 1976, pages 156, 174, 180 and 183. In certain embodiments, the elastic film may have a loading engineering stress at 200% strain (L200) of between about 0.8 and 2 MPa, 1.0 and 1.5 MPa, or even between 1.0 and 1.2 MPa, and an unloading engineering stress at 50% strain (UL50) of between 0.3 and 0.8, 0.4 and 0.6, or even between 0.5 and 0.6 MPa according to the Hysteresis Test described in more detail below. The L200 and UL50 values disclosed above may be important for providing a film that is suitable for use in a disposable absorbent article (e.g., for providing low force recovery stretch, a snug comfortable fit, less undesired sag, containment of bodily exudates in a desired location, strength to resist the initial formation of a hole or tear).

The present tear resistant films may include optional additives such as anti-oxidants and/or modifying resins. Further, the films may be physically modified (e.g., apertured, slit, incorporated into a multi-layer laminate material, or subjected to an incremental stretching process) and still demonstrate suitable tear propagation resistance. Exemplary films, including optional additives, modifying resins, and physical modifications are disclosed in the aforementioned copending application titled "Tear Resistant Film."

Laminate

In certain embodiments, it may be desirable to incorporate the film into a laminate such as, for example, a trilaminate wherein a film layer is sandwiched between two nonwoven layers (e.g., a film layer sandwiched between two SMS nonwoven layers). It is to be appreciated that the laminate may be configured to include any number of film and/or nonwoven layers, as desired. Laminates herein may have a laminate integrity time of greater than 2 hours, 5 hours, 10 hours, 20 hours, 30 hours or even greater than 50 hours, but typically less than 100 hours, when tested according to the Laminate Integrity Test set forth in co-pending U.S. Ser. No. 13/026,548, filed on Feb. 14, 2011 by Mansfield and titled "Tear Resistant Laminate". Ideally, the tear resistance laminates described herein can resist the growth of a hole, tear, or aperture indefinitely. Suitable examples of laminate structures are disclosed in the aforementioned co-pending application titled "Tear Resistant Laminate" and U.S. Publication No. 2007/0249254 filed by Mansfield on Apr. 24, 2006 and titled "Stretch Laminate, Method of Making and Absorbent Article."

Absorbent Article

In certain embodiments, the film and/or laminate may be incorporated into an article (e.g., a diaper or training pant), where it is particularly important that the article function as intended for a predetermined amount of time (e.g., through the night while the wearer sleeps). Thus, suitable laminate integrity times and time-to-fail values are important for providing an indication that an article or article component that includes the laminate or film is less likely to suffer catastrophic failure in use.

While one or more of the following exemplary embodiments may be directed to a diaper, training pant, or similar wearable absorbent article, it is to be understood that the tear resistant film disclosed herein may be practiced to great advantage with a variety of articles including, without limitation, hard surface cleaning wipes or pads; pre-moistened cloths; paper towels; dryer sheets and dry-cleaning cloths; adult incontinence briefs and undergarments; feminine hygiene garments such as panty liners, sanitary napkins, absorbent inserts, and the like; toilet paper; tissue paper; personal cleaning wipes or clothes such as baby wipes or facial wipes; packaging components and substrates and/or containers for laundry detergent and coffee, which may be produced in pellets or pouches and may be manufactured in a converting or web process.

FIG. 1 is a plan view of an exemplary, non-limiting embodiment of a diaper 20 in a flat, uncontracted state (i.e., without elastic induced contraction). The garment-facing surface 120 of the diaper 20 is facing the viewer. The diaper 20 includes a longitudinal centerline 100 and a lateral centerline 110. The diaper 20 includes a front waist region 36, a rear waist region 38 opposed to the front waist region 36, and a crotch region 37 located between the front waist region 36 and the rear waist region 38. The waist regions 36, 38 generally comprise those portions of the diaper 20 which, when worn, encircle the waist of the wearer. The waist regions 36 and 38 may include elastic elements (e.g., formed from a tear resistant film or polymer disclosed herein) that gather the material in the front and/or back waist region 36, 38 about the waist of the wearer to provide improved fit and containment. The crotch region 37 is that portion of the diaper 20 which, when the diaper 20 is worn, is generally positioned between the legs of the wearer. The outer periphery of the diaper 20 is defined by longitudinal side edges 12 and end edges 14. The opposing longitudinal side edges 12 may be oriented generally parallel to the longitudinal centerline 100. Elastic elements (e.g., formed from the tear resistant film or polymers disclosed herein) may be disposed adjacent the side edges 14 of the diaper 20 to form gasket cuffs when the diaper 20 is in a fastened configuration. In certain embodiments, elastic elements having a tear resistant polymer incorporated therein may be disposed inboard of the side edges 12 (i.e., toward the longitudinal centerline 100) to form barrier leg cuffs. Suitable examples of gasketing cuffs and barrier leg cuffs are described in U.S. Pat. No. 5,032,120, issued on Jul. 16, 1991 to Freeland, et al., and U.S. Pat. No. 7,527,616, issued on May 5, 2009 to Miyamoto.

The diaper 20 shown in FIG. 1 includes a liquid permeable topsheet 24, a liquid impermeable backsheet 26, and an absorbent core 28 disposed therebetween. The absorbent core 28 may have a body-facing surface and a garment facing-surface. The topsheet 24, the backsheet 26, and the absorbent core 28 may be assembled in a variety of well-known configurations. For example, the topsheet 24 may be joined to the core 28 and/or the backsheet 26. The backsheet 26 may be joined to the core 28 and/or the topsheet 24. It should be recognized that other structures, elements, or substrates may also be positioned in a joined or unjoined relationship between the core 28, the topsheet 24 and/or the backsheet 26. Nonlimiting examples of suitable diaper configurations are described generally in U.S. Pat. Nos. 3,860,003; 4,808,178; 4,909,803; 5,151,092; 5,221,274; 5,554,145; 5,569,234; 5,580,411; 6,004,306; and 7,626,073; and U.S. Publication No. 2007/0249254.

The topsheet 24 typically includes a portion of the diaper 20 that is positioned at least in partial contact or close proximity to a wearer. Suitable topsheets 24 may be manufactured from a wide range of materials, such as porous foams; reticulated foams; apertured films (e.g., the tear resistant film disclosed herein); or woven or nonwoven web of natural fibers (e.g., wood or cotton fibers), synthetic fibers, or a combination of natural and synthetic fibers; or multilayer laminates of these materials. Generally, at least a portion of the topsheet 24 is liquid pervious, permitting liquid to readily penetrate through the thickness of the topsheet 24. Any portion of the topsheet 24 may be coated with a lotion as is known in the art. Examples of suitable lotions include those described in U.S. Pat. Nos. 5,607,760; 5,609,587; 5,635,191; and 5,643,588.

The absorbent core 28 may comprise a wide variety of liquid-absorbent materials commonly used in disposable diapers and other absorbent articles (e.g., superabsorbent polymer particles ("SAP") and/or airfelt). These materials may be combined to provide a core 28 in the form of one or more layers, which may include fluid handling layers such as acquisition layers, distribution layers and storage layers. Such absorbent cores 28 may also include layers to stabilize other core components. Such layers may include a core cover and a dusting layer. In certain embodiments, one or more of the core layers may include a tear resistant film, as described herein. In certain embodiments, the absorbent core 28 may include less than 20 wt % of airfelt, based on weight of the absorbent core 28, or the absorbent core 28 may even be airfelt-free. Exemplary absorbent structures for use as the absorbent core 28 are described in U.S. Pat. Nos. 4,610,678; 4,673,402; 4,834,735; 4,888,231; 5,137,537; 5,147,345; 5,342,338; 5,260,345; 5,387,207; 5,397,316; and 5,625,222; 7,750,203; and 7,744,576.

The backsheet 26 may be positioned such that it includes at least a portion of the garment-facing surface 120 of the diaper 20. The backsheet 26 may be designed to prevent the exudates absorbed by and contained within the diaper 20 from soiling articles that may contact the diaper 20, such as bed sheets and undergarments. In certain embodiments, the backsheet 26 is substantially water-impermeable. One or more portions of the backsheet may be formed from the tear resistant film material disclosed herein. Other suitable backsheet 26 materials may include breathable materials that permit vapors to escape from the diaper 20 while still preventing exudates from passing through the backsheet 26. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet 26 including, but not limited to, surface treatments, particular film selections and processing, particular filament selections and processing, etc.

The backsheet 26 may also include more than one layer configured, for example, as discrete, unjoined layers or as laminate. It is to be appreciated that such laminate structures are not limited to the backsheet 26, but may be incorporated into any of the diaper 20 components described herein or commonly known in the art (e.g., ears or sides panels), as desired. As illustrated in the cut-away of FIG. 2, the backsheet 26 may include an outer cover 26a and an inner layer 26b that is at least partially disposed under the outer cover 26a, when viewed from the garment facing side of the diaper 20. The outer cover 26a may have longitudinal side edges 27a, and the inner layer 26b may have longitudinal side edges 27b. The outer cover 26a may be made of a soft, non-woven material. The inner layer 26b, or portion thereof, may be made of a substantially water-impermeable film such as the elastic, tear resistant film disclosed herein. In certain embodiments, the waist regions 36 and 38 of the inner layer 26b may include the tear resistant, elastic film material, while the crotch region 37 of the inner layer 26b includes no film or a different film. The outer cover 26a and an inner layer 26b may be joined together by adhesive or any other suitable material or method. In addition, the outer cover 26a and/or the inner cover 26b may also each include more than one layer of material such as, for example, in a laminate structure.

The diaper 20 may also include a fastening system 50. When fastened, the fastening system 50 typically interconnects the front waist region 36 and the rear waist region 38 resulting in a waist circumference that generally encircles a wearer of the diaper 20. It may be desirable to provide portions or components of the fastening system 50 with elastic extensibility. Thus, one or more portions or components of the fastening system may include a tear resistance film material, as described herein. Exemplary surface fastening systems are disclosed in U.S. Pat. Nos. 3,848,594; 4,662,875; 4,846,815; 4,894,060; 4,946,527; 5,151,092; and 5,221,274. An exemplary interlocking fastening system is disclosed in U.S. Pat. No. 6,432,098. The fastening system 50 may also provide a means for holding the article in a disposal configuration as disclosed in U.S. Pat. No. 4,963,140. The fastening system 50 may also include primary and secondary fastening systems, as disclosed in U.S. Pat. No. 4,699,622. The fastening system 50 may be constructed to reduce shifting of overlapped portions or to improve fit as disclosed in U.S. Pat. Nos. 5,242,436; 5,499,978; 5,507,736; 5,591,152; and co-pending U.S. Ser. No. 12/794,103, filed on Jun. 4, 2010 by Rezai, et al.

In certain embodiments, a portion of the fastening system 50 may be disposed on one or more of the ears 40, 42 of the diaper, which are described in more detail hereinbelow. For example, the fastening system 50 exemplified in FIG. 1, which includes an engaging member 52 and a receiving member 54, may be configured with the engaging member 52 disposed on the back ear 42. The engaging member 52 includes an engaging surface 53 that is engageable with a complementary receiving surface on the receiving member 54 and/or another portion of the diaper 20. The engaging member may be disposed on an ear 40, 42 of the diaper 20 such that it extends laterally outwardly therefrom, as depicted in FIG. 1. In certain embodiments, the engaging member 352 may be an integral part of the ear 40, 42, for example, as shown in FIG. 2.

The diaper 20 may include one or more ears 40, 42, sometimes referred to as "side panels" or "sides" when the diaper 20 (or pant) is in a fastened or pre-fastened configuration, which extend laterally outwardly from one or both side edges 12 in the front and/or back waist regions 36, 38. The ears 40, 42 may extend in the longitudinal direction from the end edge 14 of the diaper 20 to the portion of the side edge 12 of the diaper 20 that forms the leg openings 355 when the diaper 20 is in a fastened configuration, for example, as shown in FIG. 2. The ears 40, 42 may be configured as unitary elements of the backsheet, topsheet, and/or core (i.e., they are formed from and are extensions of the backsheet, topsheet, and/or core materials), or the ears 40, 42 may be separate manipulatable elements secured to the backsheet and/or topsheet by any suitable means known in the art. The ears 40, 42 may be configured as a single film layer or as a laminate structure of one or more film layers and one or more nonwoven layers. For example, the ear 40, 42 may be configured as a tear resistant film layer disposed between two nonwoven layers. Each nonwoven layer may also be configured as two or more layers. Laminates suitable for use herein have a minimum laminate integrity time of greater than 2 hours, 5 hours, 10 hours, 20 hours, 30 hours or even greater than 50 hours, but typically less than 100 hours, when tested according to the Laminate Integrity Test described in the aforementioned copending application titled "Tear Resistant Laminate." Ideally, a tear resistance laminate can resist the growth of a hole, tear, or aperture indefinitely. The laminate structure used to form an ear 40, 42 may be subjected to an incremental stretching process before or after incorporation in the ear 40, 42 or diaper 20 to activate the nonwoven layers and provide an elastically extensible ear, for example, as described U.S. Pat. No. 5,464,401 issued to Hasse, et al., on Nov. 7, 1995 and U.S. Pat. No. 4,834,741 issued to Sabee, et al., on May 30, 1989. In certain embodiments, it may be desirable to configure the ear, or portion thereof, to be breathable, for example, by providing micropores, apertures, capillaries, or other discontinuities in the film.

Figure 2:
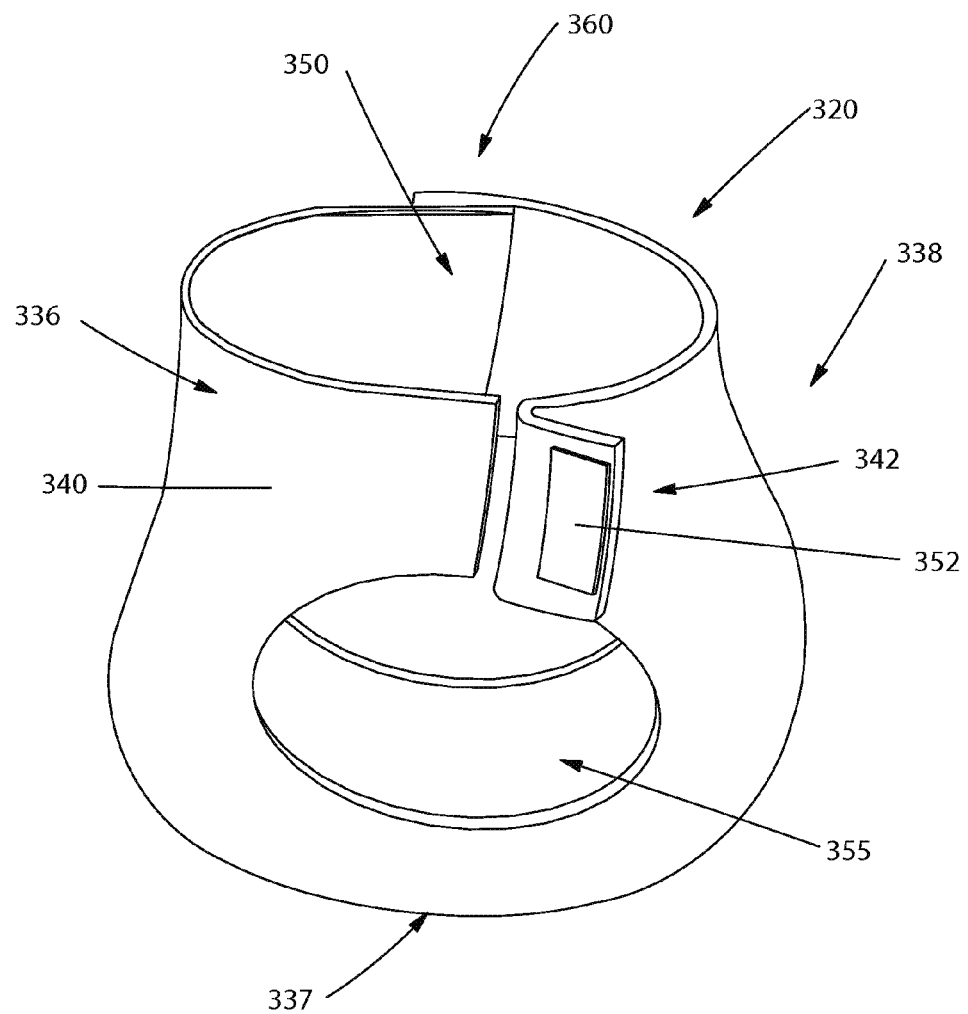
FIG. 2 is a perspective view of an absorbent article.

FIG. 2 shows a diaper 300 in a partially fastened configuration (i.e., one fastener is fastened and the other fastener is not fastened). The front and back waist regions 336 and 338 include front and back ears 340, 342 that may be permanently or refastenably joined to one another (e.g., with engaging member 352) to form a waist opening 350 that encircles the waist of a wearer when the diaper 300 is worn as intended. Disposed on the back ear 342 may be one or more components that make up a fastening system, such as the engaging member 352. The engaging member 352 engageable with another portion of the diaper 300 such as, for example, a receiving member disposed on the front ear 340 or a portion of the front waist region 336. The engaging member 352 and receiving member, if provided, may each include a surface feature that complements and is capable of forming a mechanical bond with the surface feature of the other (e.g., hooks and loops or tab and slot). The diaper 100 may include a crotch region 337 extending between the front and back waist regions 336 and 338. The front and back waist regions 336 and 338 may each include one or more elastic waist features. The fastened diaper 300 may include one or more leg openings 355 defined by a leg band region. The leg opening 355 may have a minimum hoop diameter of at least 4 cm and/or a maximum hoop diameter of at least 10 cm. The leg opening 355 may be configured to have a range of hoop diameters whereby the maximum hoop diameter is at least 3×, 5× or even 10× greater than the minimum hoop diameter.

In certain embodiments, the absorbent article may be preformed (i.e., packaged in a fastened configuration) by the manufacturer to create a pant product such as a commonly known training pant. A pant may be preformed by any suitable technique including, but not limited to, joining together portions of the article using refastenable and/or non-refastenable bonds (e.g., seam, weld, adhesive, cohesive bond, fastener, etc.). For example, the article may be manufactured with the fastening system pre-engaged (i.e., the engaging member is joined to the receiving member 54 prior to packaging the article for sale). As an additional example, the article may be manufactured with the front ears 40 joined to the back ears 42 by way of a bond such as an adhesive bond, a mechanical bond, or some other bonding technique known in the art. It may be desirable to include a wetness indicator on the pant, which provides a sensory cue (e.g., visual or audible) to indicate the presence and/or quantity of urine and/or feces in the pant (or diaper 20 described above). Suitable pants are disclosed in U.S. Pat. Nos. 5,246,433; 5,569,234; 6,120,487; 6,120,489; 4,940,464; 5,092,861; 5,897,545; and 5,957,908. Suitable wetness indicators are disclosed in U.S. Pat. No. 7,332,642, issued on Feb. 19, 2008 to Liu; U.S. Pat. No. 7,159,532, issued on Jan. 9, 2007 to Klofta, et al.; U.S. Pat. No. 7,105,715, issued on Sep. 12, 2006 to Carlucci, et al.; U.S. Pat. No. 6,904,865, issued on Jun. 14, 2005 to Klofta, et al.; and U.S. Pat. No. 6,772,708, issued on Aug. 10, 2004 to Klofta, et al.

Test Methods.

Environmental conditions for the test methods herein include a temperature of 23° C.±2° C., unless indicated otherwise. In some instances, a film sample to be tested may include one or more layers of other material joined to the film material (e.g., samples taken from commercially available articles). In such instances, the film is carefully separated from the other layers of material so that damage to the film is avoided. If the film is damaged (i.e., torn, cut, punctured, etc.) as a result of separating the film from the other material, discard the sample and obtain another that is undamaged. Basis Weight (mass per unit area)

The basis weight of each film is determined according to INDA Standard Test WSP 130.1 (09). All conditioning and testing is conducted in an atmosphere of 23±2° C., and 50±5% relative humidity.

The average of 5 specimens is reported as the Average Basis Weight in grams per square meter (gsm) to 3 significant digits.

Effective Average Thickness

The Effective Average Thickness of the film is calculated from the Average Basis Weight as follows.

Effective Average Thickness=Average Basis Weight/density

Units:

Thickness: micrometers (μm)

Basis Weight: gsm density=0.92 grams per cm$^3$ (g/cc)

Results are reported in microns (μm) to 3 Significant digits.

Hysteresis

Figure 3:
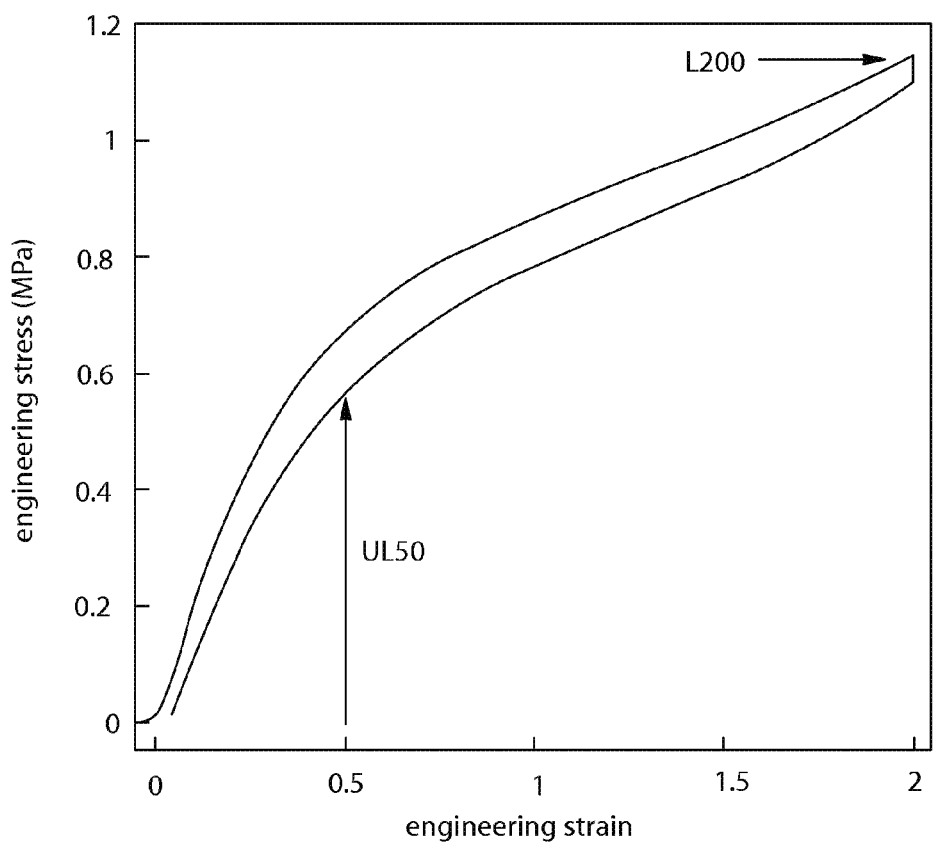
FIG. 3 is a chart of stress versus strain.

The Hysteresis test is performed in accordance with ASTM D882-02 using line-contact grips and a load-hold-unload sequence, along with the exceptions and/or conditions set forth below. FIG. 3 is provided to illustrate the portion of the stress-strain curve that includes the L200 value (i.e., the engineering stress at 200% strain during loading) and the UL50 value (i.e., the engineering stress at 50% strain during unloading) generated during the Hysteresis test. One load-unload cycle is a run.
  specimen width: 25.4 mm
  gauge length: 25.4 mm
  testing speed: 4.233 mm/s
  temperature: 22-24 C
  applied displacement: 50.8 mm (200% engineering strain)
  hold time at the applied displacement: 30 seconds
  If grip design does not accommodate the 50 mm extra sample length indicated in section 6.1 of ASTM D882-02, prepare samples to a length that allows gripping the appropriate gauge length without interfering with other parts of the grip. In such cases care must be taken to mount the specimen with proper alignment, gripping and gauge definition.
  Record the following:
  engineering stress at 200% engineering strain during the load segment (L200)
  engineering stress at 50% engineering strain during the load segment (UL50)
  engineering strain during unloading where the sample goes slack (Ls).

The set is then defined as Ls, expressed as a proportion of the engineering strain at applied displacement. For example if 200% engineering strain is applied to the sample and it goes slack at an engineering strain of 20% during unloading, the set is calculated as 20%/200%=0.10=10%.

When using the hysteresis test to determine whether a material meets the definition of "elastic" or "plastic" as described in the definitions, an applied displacement of 12.7 mm (i.e. an engineering strain of 50%) is used.

Differential Scanning Calorimetry (DSC)

Figure 4:
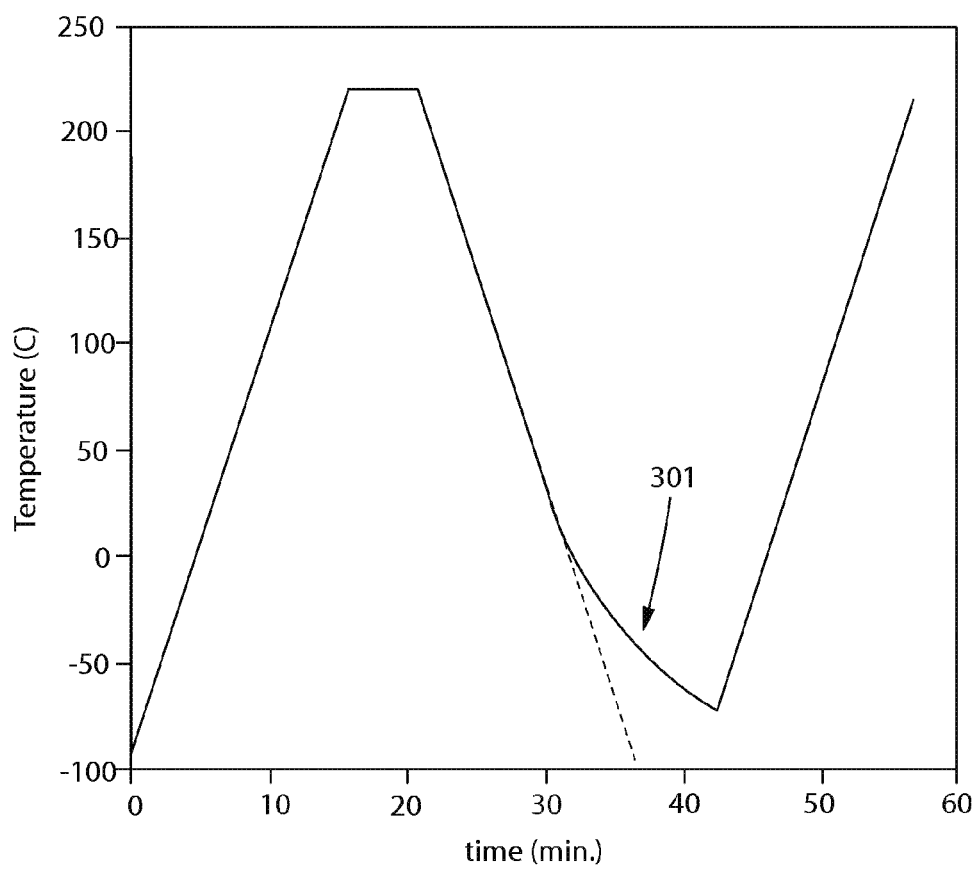
FIG. 4 is a chart of time versus temperature for use with the DSC test.

The DSC test is used to measure the melting temperature ($T_m$) of a polymer. The $T_m$ is determined by DSC measurements according to ASTM D3418-08 (note that $T_m$ is referred to as $T_{mp}$ in the ASTM method), except that the time-temperature profile shown in FIG. 4 is used for the measurement. Calibration is performed with a heating rate of 20° C./min. The temperature profile may include the non-linear portion 401 of profile at Time=30-42 minutes, as shown in FIG. 4. The non-linear portion 401 is a manifestation of limitations in the cooling capability of the apparatus. It is recognized that this deviation from the nominal cooling rate might have a modest effect on the observed melting curve, but all DSC data herein follows the same profile.

Air Permeability Test

The air permeability of a substrate (e.g., film, laminate, or article component) is determined by measuring the flow rate of standard conditioned air through a test specimen driven by a specified pressure drop. This test is particularly suited to materials having relatively high permeability to gases, such as nonwovens, apertured films and the like. ASTM D737 is used, modified as follows.

A TexTest FX3300 instrument or equivalent is used, which are available from Textest AG, Switzerland, or from Advanced Testing Instruments ATI in Spartanburg S.C., USA. The procedures described in the Operating Instructions for the TEXTEST FX 3300 Air Permeability Tester manual for the Air Tightness Test and the Function and Calibration Check are followed. If a different instrument is used, similar provisions for air tightness and calibration are made according to the manufacturer's instructions.

The test pressure drop is set to 125 Pascal and the 5 $cm^2$ area test head (model FX3300-5) is used. After making the measurement of a specimen according to the procedure given in the Operating Instructions for the TEXTEST FX 3300 Air Permeability Tester manual, the result is recorded to three significant digits. The average of 5 specimens air permeability data of this sample (in $m^3/m^2/min$) is calculated and reported as the Air Permeability Value.

EXAMPLES

Table 2 shows the formulas for making various film Samples. The S4033, JL-007, and JL-014 shown in Table 2 are hydrogenated SEEPS block copolymers available from Kuraray America, Inc. in Pasadena, Tex. S4033 is a known SEEPS block copolymer, while the JL series (e.g., JL-007 and JL-014) may be thought of as S4033-type block copolymers modified for improved processability. The JL-series of SEEPS block copolymers have a mass ratio of isoprene to 1,3 butadiene of from 46/54 to 44/56 (e.g., 45/55). The oil in Table 2 is a white mineral oil such as Drakeol 600, Hydrobrite 550, or Krystol 550. REGALREZ 1126 and REGALITE 1125 are tackifiers available from Eastman Chemical Company in Kingsport, Tenn. The PS 3190 is a polystyrene homopolymer available from NOVA Chemical Company, Canada. AO is a suitable antioxidant such as Irganox 100 available from Ciba Specialty Chemicals in Switzerland.

Samples 1-11 are produced by extruding a thermoplastic composition through a slot die to form a film that is 100 mm wide and 100 µm thick. The thermoplastic composition is formed by extruding material in a Leistritz (27 mm) twin screw extruder with extended mixing sections. First, the oil and Septon polymers are mixed together, and then the polystyrene and tackifier are blended into the mixture, which is then fed into the extruder. Temperatures in the extruder typically range from 170-230° C. Subsequently, the compositions are formed into films using a ThermoFisher 20 mm single screw extruder. Temperatures in the ThermoFisher extruder typically range from 170-230° C.

TABLE 2

| Ingre-dient | Sample # | | | | | | | | | | |
|---|---|---|---|---|---|---|---|---|---|---|---|
| | 1 | 2 | 3 | 4 | 5 | 6 | 7 | 8 | 9 | 10 | 11 |
| 4033 | | | | | | | 60 | | | | 56 |
| JL-007 | 55 | 60 | 60 | 60 | | 55 | | | 60 | 56 | |
| JL-014 | | | | | 55 | | | 60 | | | |
| Oil | 15 | 20 | 20 | 16 | 15 | 15 | 20 | 20 | 20 | 31 | 31 |
| Regalrez 1126 | 15 | 10 | 15 | 16 | 15 | | 10 | 10 | | | |
| Regalite 1125 | | | | | | 15 | | | 10 | | |
| PS 3190 | 15 | 10 | 5 | 8 | 15 | 15 | 10 | 10 | 10 | 13 | 13 |
| AO | 0.05 | | | | 0.05 | 0.05 | | | | 0.1 | 0.1 |

Table 3 illustrates the time-to-fail and melt temperatures of various elastomeric film materials. Samples 1-6 and 9-10 are provided to show suitable examples of the present film. Samples 7 and 11 are provided as comparative examples to show that not all SEEPS block copolymers necessarily provide suitable tear resistance and/or processability. The time-to-fail measurements are obtained according to the Slow Tear Test and the $T_m$ values are obtained according to the DSC method. Samples 12-15 in Table 3 are formed by a two-stage compression molding procedure where the elastomer is compressed between heated platens (215° C.) and held for a dwell time of 3 minutes using shims that give a thick sheet of elastomer (approximately 2.5 mm thick) then subsequently folding and stacking the thick film and pressing without a shim and holding for a dwell time of about 30 seconds to give a film of between 80-200 µm in thickness. The percentages of the various ingredients are all weight percentages based on the weight of the film. Sample 12 is provided as a comparative example and is formed from 56% S4033, 13% PS3160, and 31% white mineral oil. Samples 13-15 include the same relative amounts of SEEPS block copolymer, polystyrene homopolymer, and mineral oil as Sample 12, but vary in the kind of SEEPS copolymer, including the $T_m$ of the polymer, used in their formation. Sample 13 is formed using 56% JL-007. Sample 14 is formed using JL-014. Sample 15 is formed using JL-013. These ingredients are added to a small batch mixer (Haake) and mixed at 50 RPM at a temperature of 210° C. for 3 minutes. Sheets are subsequently produced by pressing between heated platens held at 210° C.

TABLE 3

| Sample No. | time-to-fail (hr.) | $T_m$ (° C.) |
|---|---|---|
| 1 | 7.2 | 17.7 |
| 2 | 8.3 | 16.1 |
| 3 | 31.5 | 15.1 |
| 4 | 17.5 | 16.2 |
| 5 | 13.7 | 14.5 |
| 6 | 11.6 | 16.6 |
| 7 | 1.6 | 2.4 |
| 8 | 9.6 | 13.9 |
| 9 | 10.2 | 15.7 |
| 10 | 0.9 | 14.6 |
| 11 | 0.3 | 1.8 |
| 12 | 0.5 | −1.0 |
| 13 | 2.1 | 13.0 |
| 14 | 0.8 | 13.0 |
| 15 | 7.0 | 18.0 |
| 1 | 7.2 | 17.7 |
| 2 | 8.3 | 16.1 |
| 3 | 31.5 | 15.1 |
| 4 | 17.5 | 16.2 |
| 5 | 13.7 | 14.5 |
| 6 | 11.6 | 16.6 |
| 7 | 1.6 | 2.4 |
| 8 | 9.6 | 13.9 |
| 9 | 10.2 | 15.7 |
| 10 | 0.9 | 14.6 |
| 11 | 0.3 | 1.8 |
| 12 | 0.5 | −1.0 |
| 13 | 2.1 | 13.0 |
| 14 | 0.8 | 13.0 |
| 15 | 7.0 | 18.0 |

As can be seen Table 3, the Samples that include the S4033 SEEPS block copolymer fail to provide a time-to-fail of about an hour or more and/or a $T_m$ of between 10 to 20° C., whereas the samples formed from the JL-series of SEEPS block copolymers provide these desired properties.

Laminates were made using films formed from the SEEPS block copolymers indicated in Table 4. The weight percents of the individual film components are based on the total weight of the film and are also shown in Table 4. The films in are formed by extrusion on lab scale extrusion equipment with a temperature profile of between 180° C. at the first barrel stage and 215° C. at the extrusion die. The films have basis weights in the range of 130 to 140 gsm. A hot melt adhesive (e.g., product code 2031 available from Bostik) is applied in a spiral pattern to sheets of release paper having sufficient dimensions to cover the nonwoven and form the laminate samples described below. The adhesive is applied at a basis weight of 6.2 gsm via a spray melt process. The adhesive is transferred from the release paper to a first nonwoven material (16.5 gsm SMS nonwoven available from Fibertex under product no. ESM0337) by placing the nonwoven on the release paper and lightly pressing down on the nonwoven with moderate hand pressure to ensure good contact between the nonwoven and adhesive. The nonwoven is then carefully peeled from the release paper to transfer the adhesive from the release paper to the nonwoven. This process is repeated so that the adhesive is applied to the same side of the nonwoven twice. After removing the nonwoven from the release paper a second time, the adhesive containing side of the nonwoven is then placed on the film to adhere the nonwoven to the film. The process of applying adhesive to a nonwoven is then repeated on a second, identical nonwoven material. The second nonwoven material is then adhered to the opposite side of the film (i.e., one layer of nonwoven for each of the opposing surfaces of the film). Ensure that the nonwoven and film machine directions are coincident. The laminates are trimmed to a length and width of 100 mm and 50.8 mm, respectively. All samples are than stacked in the same stack and subjected to a pressure of 20 kPa for three seconds. Each laminate is then subjected to an activation process where the laminate is activated to an 8 mm depth-of-engagement on 200-pitch ring roll plates, wherein the teeth have a tip radius of 120 µm. In this way, 250% engineering strain is applied to the laminate in 0.2 seconds along the machine direction of the laminate to each span of material positioned between each pair of teeth. This causes permanent deformation of the nonwoven. Thus, the elastomeric film is able to stretch with substantially reduced mechanical interference from the nonwoven (relative to a non-activated laminate).

TABLE 4

| No. | Sample ID | S4033 | JL013 | PS 3190 | DRAKEOL 600 |
|---|---|---|---|---|---|
| 1 | grf410-17a | 0.56 | | 0.13 | 0.31 |
| 2 | grf410-17c | | 0.56 | 0.13 | 0.31 |

Table 5 illustrates the laminate integrity times and time-to-fail of the laminates from Table 4 when tested according to the Laminate Integrity Test.

TABLE 5

| No. | Sample ID | laminate integrity time (hr.) | Time-to-fail |
|---|---|---|---|
| 1 | GRF410-17a | 1.85 | 0.36 |
| 2 | GRF410-17c | 5.20 | 1.7 |

As can be seen from Table 5, Sample 2 exhibits a suitable laminate integrity time of greater than 2 hours. In contrast, Sample 1, which is provided as a comparative example, does not exhibit a suitable laminate integrity time of greater than 2 hours. Similarly, Sample 1 does not provide a suitable Time-to-fail of greater than 1 hour.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Additionally, properties described herein may include one or more ranges of values. It is to be understood that these ranges include every value within the range, even though the individual values in the range may not be expressly disclosed.

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A disposable absorbent article comprising an elastic film material that resists the growth of a tear, wherein the elastic film material has a High Speed Tensile Strength of between about 15 and about 22 MPa according to the High Speed Tensile Test, a time-to-fail of greater than 1 hour according to the Slow Tear Test, an Average Effective Thickness of from about 1 μm to about 1 mm and wherein the elastic film material further comprises a $T_m$ of between about 10° C. and about 20° C.

2. The disposable absorbent article of claim 1, wherein the elastic film material comprises an SEEPS block copolymer.

3. The disposable absorbent article of claim 1, wherein the elastic film material has a time-to-fail of greater than 12 hours.

4. The disposable absorbent article of claim 1, wherein the elastic film material has a time-to-fail of greater than 24 hours.

5. The disposable absorbent article of claim 1, wherein the elastic film material has a High Speed Notched Tensile Strength of between about 10 and about 20 MPa according to the Notched High-Speed Tensile Strength Test.

6. The disposable absorbent article of claim 1, wherein the elastic film material is incorporated into a component of the disposable absorbent article selected from the group consisting of a topsheet, a backsheet, an outer cover, a cuff, a side panel, an ear, a fastener, and combinations of these.

7. The disposable absorbent article of claim 6, wherein the component is breathable.

8. The disposable absorbent article of claim 1, wherein the elastic film material includes apertures.

9. The disposable absorbent article of claim 1, wherein the article is refastenable.

10. The disposable article of claim 1, wherein the elastic film is joined to one or more nonwoven layers to form a laminate.

11. The disposable article of claim 10, wherein the laminate has a Laminate Integrity Time of greater than 2 hours according to the Laminate Integrity Test.

12. A disposable absorbent article for wearing about the lower torso of a wearer, the absorbent article comprising:
   a topsheet, a backsheet, and an absorbent core disposed therebetween, first and second opposing longitudinal side edges, a front waist region and an opposing back waist region;
   a first ear extending outwardly from the first longitudinal side edge in the back waist region and joined to at least one of the topsheet, the backsheet, and the absorbent core;
   a second ear extending outwardly from the second longitudinal side edge in the back waist region and joined to at least one of the topsheet, the backsheet, and the absorbent core;
   at least one of the first and second ears comprising a laminate comprising an elastic film material that resists the growth of a tear disposed between two nonwoven layers;
   wherein at least a portion of one of the two nonwoven layers is activated and the laminate has a laminate integrity time of greater than 2 hours according to the Laminate Integrity Test; and
   wherein the elastic film material has an Average Effective Thickness of from about 1 μm to about 1 mm and a time-to-fail of greater than 1 hour according to the Slow Tear Test.

13. The disposable absorbent article of claim 12, wherein at least one of the first and second ears is breathable.

14. The disposable absorbent article of claim 12, wherein the disposable absorbent article is a prefastened pant.

15. The disposable absorbent article of claim 14, further comprising at least one refastenable fastener.

16. The disposable absorbent article of claim 14, further comprising a wetness indicator.

\* \* \* \* \*